United States Patent

Chan et al.

[11] Patent Number: 5,144,050
[45] Date of Patent: Sep. 1, 1992

[54] RUTHENIUM(II)-BINAP DIKETONATE COMPLEXES

[75] Inventors: Albert S. C. Chan, St. Louis; Scott A. Laneman, Creve Coeur, both of Mo.

[73] Assignee: Monsanto Company, St. Louis, Mo.

[21] Appl. No.: 769,277

[22] Filed: Oct. 1, 1991
(Under 37 CFR 1.47)

[51] Int. Cl.$^5$ .............................................. C07F 15/00
[52] U.S. Cl. ..................... 556/20; 556/136; 556/21
[58] Field of Search ............ 556/20, 21, 16, 136, 556/23

[56] References Cited

U.S. PATENT DOCUMENTS

| | | | |
|---|---|---|---|
| 4,691,037 | 9/1987 | Yoshikawa et al. | 556/23 X |
| 4,739,084 | 4/1988 | Takaya et al. | 556/21 |
| 4,987,242 | 1/1991 | Khanna et al. | 556/21 X |
| 4,994,590 | 2/1991 | Takaya et al. | 556/136 X |

*Primary Examiner*—Arthur C. Prescott
*Attorney, Agent, or Firm*—Charles E. Smith; Kenneth D. Goetz; Paul L. Passley

[57] ABSTRACT

Ru(BINAP) diketonate complexes manifest asymmetric hydrogenation catalytic activity with high reaction and conversion rates.

10 Claims, No Drawings

RUTHENIUM(II)-BINAP DIKETONATE COMPLEXES

BACKGROUND OF THE INVENTION

1. Field of the Invention

The present invention relates to ruthenium(II)-BINAP complexes and, more particularly, relates to ruthenium(II)-BINAP diketonate complexes. The subject Ru(II)-BINAP complexes are particularly suitable as asymmetric hydrogenation catalysts.

2. Related Art

Ruthenium(II)-BINAP complexes with $ClO_4$, $BF_4$, $PF_6$, triethylamine and diacetate ($[OAc]_2$) are known. See, for example, U.S. Pat. Nos. 4,766,225; 4,691,037; and EP272,787. However, the synthesis of such complexes is extremely tedious and expensive and produces a mixture of complex species along with impurities which are difficult to remove. For example, Ru(BINAP)(OAc)$_2$ is produced from $[Ru(II)(COD)Cl_2]_n$, (wherein COD represents cyclooctadiene) which is much more expensive than Ru(III) species such as $RuCl_3$. In addition, the product yields are quite low (50-68%). See Inorgan. Chem., 1988, 27, 566-569.

SUMMARY OF THE INVENTION

The present invention provides a new and inexpensive Ru(II)-BINAP complex based on reduction of a Ru(III) species, such as Ru(acac)$_3$ utilizing a reducing agent, such as, for example, zinc dust, in the presence of a BINAP ligand. Utilizing this method, essentially a single species is produced relatively inexpensively. The subject complexes can also be produced from known Ru(II)-BINAP complexes, e.g.[Ru(BINAP)](BF$_4$)$_2$, by reacting such known complexes with a suitable diketone. Although production of the subject catalysts in this way is more expensive and produces a variety of complexes, such catalysts are significantly more active in terms of reaction rate and percent conversion of substrate. Thus, the subject Ru(II)-BINAP diketonate complexes, independent of the manner in which they are produced, manifest asymmetric hydrogenation catalytic activity which is significantly greater than prior art complexes in terms of reaction rate as well as percent conversion of substrate.

DETAILED DESCRIPTION OF THE INVENTION

The catalysts of the present invention can be represented by the formula Ru(BINAP)(X)$_n$(Y)$_m$, wherein n is either 1 or 2; m represents an integer determined by the formula 2−n; and X and Y independently represent diketonates, chelating ligands and nonchelating anionic ligands, provided that at least one of X and Y is a diketonate anion.

As utilized herein, the term "BINAP" refers to 2,2'-bis(diarylphosphino)-1,1'-binaphthyl compounds. Examples of such compounds include 2,2'-bis(diphenylphosphino) -1-1'-binaphthyl; 2,2'-bis (di-p-tolylphosphino)-1,1'-binaphthyl; 2,2'-bis (di-p-t-butylphenylphosphino)-1,1'binaphthyl and the like.

The term "nonchelating anionic ligands" as utilized herein refers to negatively charge ligands which do not form a chelate (i.e., having two or more atoms attached) with the Ru-BINAP complex. Examples of such ligands include halides such as I, Br, Cl and F, $ClO_4$, $BF_4$, $PF_6$, and the like.

The term "chelating ligands" as utilized herein refers to ligands which form a chelate with the Ru-BINAP to form a complex. Examples of such ligands include acetate (OAc), and the like.

In certain instances, the substrate that is to be hydrogenated can participate as a ligand, either nonchelating or chelating, as well. See Example 4.

The term "diketone" as utilized herein refers to compounds of the formula:

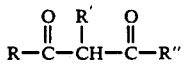

wherein R, R' and R" independently represent hydrogen, and substituted and nonsubstituted alkyl, cycloalkyl, aryl, aralkyl, alkaryl, and the like radicals. Where such radicals are substituted, substituents can include halogen, sulfones and sulfoxides, alkoxides, carboxyl, silyl, amino, and the like. Examples of such diketones include, but are not limited to the following: acetylacetonate (acac); 1,1,1-trifluoro-2,4-pentadione (tfpd); 1,1,1,16,16,16-hexafluoro-2,4,13,15-hexadecatetraone; 2,4-dioxo-1-pentanesulfonic acid; 2,4-dioxoheptanedioc acid, diethyl ester; 2-methoxy-2-methyl-3,5-tridecanedione; 4,6-dioxononanoic acid; 4,6-dioxoheptanitrile; 10-hydroxy-1,1-dimethyl-3,5-decanedione; (R)-7-([(1,1dimethylethyl)dimethylsilyl]oxy]-3,5-octanedione; (-)-1,1,1,2-tetrafluoro-2-heptafluoropropyl-6,6-dimethyl-3,5-heptanedione; 1-methoxy-2,4-heptanedione; 1-methoxy7-octene-2,4-dione; 1,1-diethyoxy-2,4-pentadione; 1,1,1-trifluoro-3,5-heptanedione; N,N-diethyl-5-methyl -2,4-dioxohexanamide; 1,1',1"-tris(2,4-pentadione)methylsilylidyne; 1-dimethylacetal-6-methyl-2,4-dioxoheptanal; [R-(R*,S*)]-7,9-dimethyl -8-(trimethylsilyl)oxy-2,4-decanedione; 2,4-pentanedione -1,1,1-d$_3$; 5,5-dimethyl-2,4-hexanedione-1-$^{13}$C; 6-hydroxy-8-methyl-2,4-nonanedione; (R)-6-acetyloxy-2,4-heptanedione; (+)-3-(trifluoroacetyl)camphor and the (−)-isomer; 1,5-bis(dimethylamino)-2,4-pentanedione; [S-R*,R*)]-3,7-dimethyl-4,6-nonanedione and the like. Other suitable diketones are well known to those skilled in the art and can also be utilized in the complexes of the present invention.

Specific examples of catalysts of the present invention include:

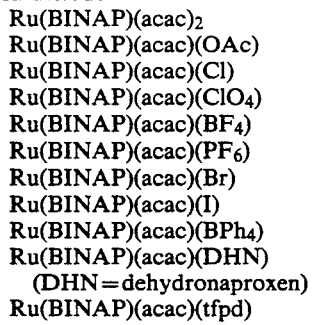

(DHN=dehydronaproxen)

Ru(BINAP)(acac)(tfpd)

The subject complexes, wherein X and Y both represent a diketonate, can be prepared by reacting a Ru(III) species such as Ru(diketonate)$_3$ (which is produced from RuCl$_3$ and the desired diketonate or desired diketone mixture in the presence of a base) with a reducing agent such as zinc dust in the presence of a BINAP ligand and in a suitable solvent, such as ethanol. Other suitable reducing agents include hydride reagents. Other suitable solvents include other alcohols such as propanol, butanol, etc. The resulting catalyst complex can be utilized as is or, for catalyst complexes wherein X and Y represent different diketonates, reacted with a diketonate anion other than that utilized to prepare the Ru(diketonate)$_3$ starting material.

The subject catalyst can also be prepared by reacting a diketone salt with a catalyst prepared by reacting a ruthenium-anion complex, e.g., ruthenium chloride, ruthenium bromide, ruthenium iodide, ruthenium fluoride and the like, including mixtures thereof, with cycloocta-1,5-diene (COD) in a suitable solvent to form [RuXY(COD)]$_n$, which is then reacted with a BINAP compound with heat (such as at reflux temperature of the solvent) and in a suitable solvent system. Suitable solvents for reacting the Ru-anion complex with COD include ethanol, propanol, isopropanol and the like. Suitable solvent systems for reacting [RuXY(COD)]$_n$ with a BINAP compound include organic acid solvents include acetic acid, propionic acid, butyric acid and the like, including mixtures thereof. Such organic acid solvents can also be combined with nonpolar organic solvents such as arene solvents, examples of which include benzene, toluene and the like, including mixtures thereof. When the solvent system is a mixture of an organic acid and a nonpolar organic solvent, such mixture can be in the range of from 1:10 to 10:1 organic aid to nonpolar solvents. Preferably, the mixture is 1:1. The catalyst prepared as described above is then reacted with one equivalent of the desired diketone in a suitable solvent system.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

The present invention also relates to a method of asymmetrically hydrogenating an olefinic substrate utilizing one or more of the complexes described above.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

Optical yields were determined by either a standard optical rotation procedure or by chiral gas chromatography of the corresponding menthol (commercially available (+)-isomer obtained from Sigma-Aldrich) ester derivatives utilizing a CHIRASIL-VAL-L column obtained from Chrompack. GC analysis was conducted utilizing a Varian 3700 gas chromatograph.

EXAMPLE 1

Preparation of Ru(acac)$_2$(S-BINAP)

A Fischer-Porter bottle was charged with 1.007 g of Ru(acac)$_3$ (2.513 mmole), 1.575 g of S-BINAP (2.528 mmole), 3.28 g of activated Zn dust, and 40 mL of degassed 95% EtOH. The mixture was stirred with a magnetic stirrer at 80° C. for 15 hours. The solvent was evaporated in vacuo. $^{31}$P NMR of the residue showed that the reaction had proceeded to virtual completion (>98%). The residue was dissolved in 70 mL of $CH_2Cl_2$ and filtered. The solvent of the clear red filtrate was removed in vacuo and 2.2 g of the Ru(acac)$_2$(S-BINAP) was obtained.

EXAMPLE 2

Asymmetric Hydrogenation of 2-methyl-2-hexenoic acid with Ru(S-BINAP)(acac)$_2$ as catalyst A catalyst solution containing 1.1 mg Ru(S-BINAP(acac)$_2$ in 0.35 g $CH_2Cl_2$ was stirred well with 0.58 g 2-methyl-2-hexenoic acid in 2.5 g $CH_3OH$ and 1 g $H_2O$ under 50 psig $H_2$ at 80° C. for 14 hours. Analysis of the final product indicated 100% conversion of the 2-methyl-2-hexenoic acid to 2-methyl-2-hexanoic acid in which 91% of the product was the S-isomer. (82% e.e.)

EXAMPLE 3

Asymmetric Hydrogenation of Dehydronaproxen

A reaction solution was prepared by mixing 0.096 g of a catalyst solution, which was prepared by dissolving .12 mg Ru(S-BINAP)(acac)$_2$ in 10.098 g $CH_2Cl_2$, to 0.307 g dehydroxynaproxen in 9.6 g $CH_3OH$ (Sub/Cat=10,000). The final solution was stirred well with a magnetic stirrer in an autoclave under 1500 psig $H_2$ at 0° C. for 6.5 hours. Analysis of the final product indicated 100% conversion of the dehydroxynaproxen to S-naproxen (94% e.e.). (Note: The S-BINAP used in this study was 98% pure, according to the vendor, Strem Chemicals).

EXAMPLE 4

When a solution containing Ru(BINAP)(acac)$_2$ (catalyst) and dehydronaproxen (substrate in methanol solvent) was allowed to stand at ambient temperature under an inert atmosphere (such as $N_2$) for a day or longer, the resulting catalyst became substantially more active in the hydrogenation reaction. For example, when a freshly prepared methanol solution of Ru(BINAP)(acac)$_2$ catalyst was used in the hydrogenation of dehydronaproxen (substrate/catalyst=10,000) at ambient temperature under 1000 psig $H_2$, only 20% conversion was observed in 30 minutes. However, if the catalyst had been "aged" with the substrate in methanol for 12 hours, the subsequent rate of hydrogenation became much faster: a complete conversion was achieved in less than 5 minutes. An NMR study revealed that when Ru(BINAP)(acac)$_2$ was mixed with dehydronaproxen in methanol solvent, a new catalyst, Ru(BINAP)(acac)(DHN), (DHN=dehydronaproxen), was formed. This new catalyst was found to be more active than all previously known homogenous catalysts for the asymmetric hydrogenation of dehydronaproxen. Some examples of the comparison of this new catalyst with other well known catalysts in the hydrogenation of dehydronaproxen are summarized in Table 1.

TABLE 1

A Comparison of the Rates of the Catalytic Hydrogenation of Dehydronaproxen

| Catalyst | Reaction Temperature (°C.) | Reaction Time (minutes) | % Conversion of Substrate to Product |
|---|---|---|---|
| Ru(S—BINAP) (acac)$_2$ (aged in methanol with DHN for 3 days) | 22 | 5 | 100 |
| Ru(S—BINAP) (OAc)$_2$ | 22 | 30 | 36 |
| Ru$_2$Cl$_4$(S—BINAP)$_2$—(NEt$_3$) | 22 | 30 | 26 |
| Ru(S—BINAP) (acac)$_2$ (aged in methanol with DHN for 3 days) | 0 | 60 | 80 |
| Ru(S—BINAP) (OAc)$_2$ | 0 | 60 | 5 |
| Ru$_2$Cl$_4$(S-BINAP)$_2$—(NEt$_3$) | 0 | 60 | 4 |

Conditions:
PH$_2$ = 1000 psig;
Solvent = methanol;
substrate/catalyst = 10,000

EXAMPLE 5

The new, highly active catalyst can also be prepared by reacting other Ru(BINAP) catalysts such as Ru(BINAP)(OAc)$_2$, Ru$_2$CL$_4$(BINAP)$_2$(NEt$_3$), [Ru(BINAP)]$^{2+}$, and the like, with one equivalent of an acetylacetonate salt, e.g.,

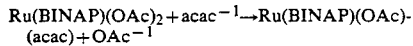

This reaction was confirmed by NMR studies and the increased catalyst activity was reflected in the effect of added acetylacetonate salts to the otherwise less active catalyst systems. Illustrative examples of this effect are summarized in Table 2.

TABLE 2

Effect of Acetylacetonate on the Rate of Ru(BINAP)-Catalyzed Hydrogenation of Dehydronaproxen

| Catalyst | Additive | Reaction Time | % Conversion |
|---|---|---|---|
| Ru(S—BINAP) (OAc)$_2$ | None | 10 | 10 |
| Ru(S—BINAP) (OAc)$_2$ | None | 30 | 36 |
| Ru(S—BINAP) (OAc)$_2$ | Zn(acac)$_2$ (½ eq.) | 30 | 100 |
| Ru(S—BINAP) (OAc)$_2$ | K(acac) | 30 | 100 |
| Ru(S—BINAP) (OAc) (acac) | None | 5 | 100 |

Conditions:
Substrate/catalyst = 10,000;
Reaction Temperature = 22° C.;
Solvent = methanol;
PH$_2$ = 1000 psig These results demonstrate that a Ru(BINAP) catalyst containing one diketone ligand, such as an acetylacetonate ligand is significantly improved over other Ru(BINAP) species in terms of rate of conversion.

While the invention has been described in detail and with reference to specific embodiments thereof, it will be apparent to one skilled in the art that various changes and modifications can be made therein without departing from the spirit and scope thereof.

WHAT IS CLAIMED IS:

1. A ruthenium phosphine diketonate complex represented by the formula:

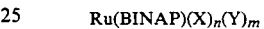

wherein
n represents 1 and 2;
m represents an integer determined by the formula 2−n; and
X and Y independently represent diketones, chelating ligands and nonchelating anionic ligands; provided that at least one of X and Y represents a diketonate anion.

2. The complex of claim 1 wherein both X and Y represent a diketonate anion.

3. The complex of claim 1 wherein n is 1, m is 1, and one of X and Y represents a diketonate and the other represents a chelating ligand.

4. The complex of claim 1 wherein n is 1, m is 1, and one of X and Y represents a diketonate and the other represents a nonchelating anionic ligand.

5. The complex of claim 1 wherein X is a diketonate and n is 2.

6. Method of preparing a complex of claim 1 or 5 comprising reacting a Ru(III) diketonate species with a reducing agent in the presence of a BINAP ligand.

7. Method of preparing a catalyst of claim 3 comprising reacting a Ru(BINAP) complexed with a chelating ligand with one equivalent of a diketonate.

8. Method of preparing a catalyst of claim 4 comprising reacting a Ru(BINAP) complexed with a nonchelating anionic ligand with one equivalent of a diketonate.

9. Method of preparing a complex of claim 5 comprising reacting a Ru(III) diketonate species with a reducing agent in the presence of a BINAP ligand.

10. Method for hydrogenating an olefinic substrate comprising hydrogenating said substrate in the presence of a complex of claim 1.

* * * * *